(12) United States Patent
Yaacobi

(10) Patent No.: US 6,986,900 B2
(45) Date of Patent: Jan. 17, 2006

(54) OPHTHALMIC DRUG DELIVERY DEVICE

(75) Inventor: Yoseph Yaacobi, Forth Worth, TX (US)

(73) Assignee: Alcon, Inc., Hunenberg (CH)

( * ) Notice: Subject to any disclaimer, the term of this patent is extended or adjusted under 35 U.S.C. 154(b) by 0 days.

(21) Appl. No.: 10/702,210

(22) Filed: Nov. 5, 2003

(65) Prior Publication Data

US 2004/0092911 A1 May 13, 2004

Related U.S. Application Data

(63) Continuation of application No. PCT/US02/23116, filed on Jul. 22, 2002.

(60) Provisional application No. 60/307,226, filed on Jul. 23, 2001.

(51) Int. Cl.
A61F 2/14 (2006.01)

(52) U.S. Cl. .................................... 424/427
(58) Field of Classification Search ................ 424/427
See application file for complete search history.

(56) References Cited

U.S. PATENT DOCUMENTS

| | | |
|---|---|---|
| 3,416,530 A | 12/1968 | Ness |
| 3,828,777 A | 8/1974 | Ness |
| 4,014,335 A | 3/1977 | Arnold |
| 4,300,557 A | 11/1981 | Refojo et al. |
| 4,327,725 A | 5/1982 | Cortese et al. |
| 4,624,848 A | 11/1986 | Lee |
| 4,853,224 A | 8/1989 | Wong |
| 4,946,450 A | 8/1990 | Erwin |
| 4,997,652 A | 3/1991 | Wong |
| 5,147,647 A | 9/1992 | Darougar |
| 5,164,188 A | 11/1992 | Wong |
| 5,178,635 A | 1/1993 | Gwon et al. |
| 5,300,114 A | 4/1994 | Gwon et al. |
| 5,322,691 A | 6/1994 | Darougar et al. |
| 5,378,475 A | 1/1995 | Smith et al. |
| 5,403,901 A | 4/1995 | Namdaran et al. |
| 5,443,505 A | 8/1995 | Wong et al. |
| 5,466,233 A | 11/1995 | Weiner et al. |
| 5,466,466 A | 11/1995 | Muller |
| 5,476,511 A | 12/1995 | Gwon et al. |
| 5,516,522 A | 5/1996 | Peyman et al. |
| 5,632,984 A | 5/1997 | Wong et al. |
| 5,679,666 A | 10/1997 | Clark |
| 5,710,165 A | 1/1998 | Kapin et al. |
| 5,725,493 A | 3/1998 | Avery et al. |
| 5,743,274 A | 4/1998 | Peyman |

(Continued)

FOREIGN PATENT DOCUMENTS

DE 40 22 553 1/1992

(Continued)

OTHER PUBLICATIONS

"Bausch & Lomb and Control Delivery Systems Agree to Develop Breakthrough Therapeutic Products for Severe Eye Diseases;" Business Wire Via First!; NewsEdge Corp.; Jun. 15, 1999; 4 pp.

(Continued)

Primary Examiner—Carlos A. Azpuru
(74) Attorney, Agent, or Firm—W. David Lee

(57) ABSTRACT

An ophthalmic drug delivery device having a scleral surface, an orbital surface, an injection port on the orbital surface, and a fluid conducting passageway disposed within the device that is fluidily coupled to the injection port and terminates in an opening for communicating the fluid to an outer surface of the sclera is disclosed. The fluid contains a pharmaceutically active agent useful for the treatment of a disease of the posterior segment of the eye.

13 Claims, 8 Drawing Sheets

U.S. PATENT DOCUMENTS

| | | | |
|---|---|---|---|
| 5,766,242 | A | 6/1998 | Wong et al. |
| 5,766,619 | A | 6/1998 | Aiache et al. |
| 5,770,592 | A | 6/1998 | Clark |
| 5,773,019 | A | 6/1998 | Ashton et al. |
| 5,797,898 | A | 8/1998 | Santini, Jr. et al. |
| 5,824,072 | A | 10/1998 | Wong |
| 5,824,073 | A | 10/1998 | Peyman |
| 5,830,173 | A | 11/1998 | Avery et al. |
| 5,836,935 | A | 11/1998 | Ashton et al. |
| 5,902,598 | A | 5/1999 | Chen et al. |
| 5,904,144 | A | 5/1999 | Hammang et al. |
| 5,916,584 | A | 6/1999 | O'Donoghue |
| 6,001,386 | A | 12/1999 | Ashton et al. |
| 6,074,661 | A | 6/2000 | Olejnik et al. |
| 6,110,485 | A | 8/2000 | Olejnik et al. |
| 6,120,460 | A | 9/2000 | Abreu |
| 6,126,687 | A | 10/2000 | Peyman |
| 6,146,366 | A | 11/2000 | Schachar |
| 6,217,895 | B1 | 4/2001 | Guo et al. |
| 6,375,972 | B1 | 4/2002 | Guo et al. |
| 6,378,526 | B1 | 4/2002 | Bowman et al. |
| 6,397,849 | B1 | 6/2002 | Bowman et al. |
| 6,413,245 | B1 | 7/2002 | Yaacobi et al. |
| 6,413,540 | B1 | 7/2002 | Yaacobi |
| 6,416,777 | B1 | 7/2002 | Yaacobi |
| 6,669,950 | B2 | 12/2003 | Yaacobi |
| 6,713,081 | B2 | 3/2004 | Robinson et al. |
| 6,719,750 | B2 | 4/2004 | Varner et al. |
| 2002/0188282 | A1 | 12/2002 | Greenberg |
| 2003/0175324 | A1 | 9/2003 | Robinson et al. |
| 2004/0180075 | A1 | 9/2004 | Robinson et al. |
| 2004/0219181 | A1 | 11/2004 | Viscasillas |

FOREIGN PATENT DOCUMENTS

| | | |
|---|---|---|
| EP | 0 904 787 | 3/1999 |
| RU | 2149615 | 5/2000 |
| WO | WO 94/05257 | 3/1994 |
| WO | WO 95/26734 | 10/1995 |
| WO | WO 95/28984 | 11/1995 |
| WO | WO 96/36377 | 11/1996 |
| WO | WO 97/14415 | 4/1997 |
| WO | WO 98/23228 | 6/1998 |
| WO | WO 98/43611 | 10/1998 |
| WO | WO 99/07418 | 2/1999 |
| WO | WO 99/11244 | 3/1999 |
| WO | WO 99/32104 | 7/1999 |
| WO | WO 99/45920 | 9/1999 |
| WO | WO 00/56340 | 3/2000 |
| WO | WO 00/37066 | 6/2000 |
| WO | WO 01/49226 | 7/2001 |
| WO | WO 02/100318 | 2/2002 |

OTHER PUBLICATIONS

"Method of Placing Irrigation System into Tenon's Space," E.I. Sidorenko, et al., Abstract of Russian Patent No. RU 2123314, issued Dec. 20, 1998, 1 pg.

"A New method for Posterior Sub-Tenon's Drug Administration," NESTEROV, et al., Ophthalmic Surgery, vol. 24, No. 1, Jan. 1993, pp. 59-61.

DIALOG File 266:FEDRIP database record; Identifying No. 122098; "Implantation of a Sub-Tenon Drug Delivery Device Loaded with a Test Article in Rabbits and Distribution of the Test Article in Ocular Tissues;" Compiled and distributed by NTIS; 1 page; Jun. 3, 1999.

DIALOG File 266: FEDRIP database record; Identifying No. 134284; "Implantation of a Sub-Tenon Drug Delivery Device Loaded with a Test Article in Rabbits and Distribution of the Test Article in Ocular Tissues;" Compiled and distributed by NTIS; 1 page.

DIALOG File 266: FEDRIP database record; Identifying No. 131476; Ocular Bioavailability of AL-3789 and AL-4940 after Sub-Tenon's Injection of AL-3789 Ophthalmic Suspensions in New Zealand White Rabbits; Compiled and distributed by NTIS; 1 page.

OPHTHALMIC DRUG DELIVERY DEVICE

This application is a continuation of PCT/US02/23116 filed Jul. 22, 2002 entitled "Ophthalmic Drug Delivery Device," which claims priority from U.S. Provisional Application No. 60/307,226, filed Jul. 23, 2001. This application is related to U.S. Pat. Nos. 6,413,540 and 6,416,777, both of which are incorporated herein in their entirety by this reference.

FIELD OF THE INVENTION

The present invention generally pertains to biocompatible implants for delivery of pharmaceutically active agents to the eye. More particularly, but not by way of limitation, the present invention pertains to biocompatible implants for delivery of pharmaceutically active agents to the posterior segment of the eye.

DESCRIPTION OF THE RELATED ART

Several diseases and conditions of the posterior segment of the eye threaten vision. Age related macular degeneration (ARMD), choroidal neovascularization (CNV), retinopathies (e.g., diabetic retinopathy, vitreoretinopathy), retinitis (e.g., cytomegalovirus (CMV) retinitis), uveitis, macular edema, glaucoma, and neuropathies are several examples.

Age related macular degeneration (ARMD) is the leading cause of blindness in the elderly. ARMD attacks the center of vision and blurs it, making reading, driving, and other detailed tasks difficult or impossible. About 200,000 new cases of ARMD occur each year in the United States alone. Current estimates reveal that approximately forty percent of the population over age 75, and approximately twenty percent of the population over age 60, suffer from some degree of macular degeneration. "Wet" ARMD is the type of ARMD that most often causes blindness. In wet ARMD, newly formed choroidal blood vessels (choroidal neovascularization (CNV)) leak fluid and cause progressive damage to the retina.

In the particular case of CNV in ARMD, three main methods of treatment are currently being developed, (a) photocoagulation, (b) the use of angiogenesis inhibitors, and (c) photodynamic therapy. Photocoagulation is the most common treatment modality for CNV. However, photocoagulation can be harmful to the retina and is impractical when the CNV is near the fovea. Furthermore, over time, photocoagulation often results in recurrent CNV. Oral or parenteral (non-ocular) administration of anti-angiogenic compounds is also being tested as a systemic treatment for ARMD. However, due to drug-specific metabolic restrictions, systemic administration usually provides sub-therapeutic drug levels to the eye. Therefore, to achieve effective intraocular drug concentrations, either an unacceptably high dose or repetitive conventional doses are required. Periocular injections of these compounds often result in the drug being quickly washed out and depleted from the eye, via periocular vasculature and soft tissue, into the general circulation. Repetitive sub-Tenon's capsule injections of these compounds carry the potential risk of penetrating the globe and the severe, often blinding, complications of retinal detachment and endophthalmitis. In addition, it is difficult to perform such injections in a reproduceable manner, and each injection may result in a different distribution of drug along the scleral surface. Furthermore, many attempts to inject drug below the Tenon's capsule actually result in injections into the Tenon's capsule itself or the surrounding tissue, which is not desirable. Repetitive intraocular injections may also result in retinal detachment and endophthalmitis. Photodynamic therapy is a new technology for which the long-term efficacy is still largely unknown.

In order to prevent complications related to the above-described treatments and to provide better ocular treatment, researchers have suggested various implants aimed at delivery of anti-angiogenic compounds to the eye. U.S. Pat. No. 5,824,072 to Wong discloses a non-biodegradable polymeric implant with a pharmaceutically active agent disposed therein. The pharmaceutically active agent diffuses through the polymer body of the implant into the target tissue. The pharmaceutically active agent may include drugs for the treatment of macular degeneration and diabetic retinopathy. The implant is placed substantially within the tear fluid upon the outer surface of the eye over an avascular region, and may be anchored in the conjunctiva or sclera; episclerally or intrasclerally over an avascular region; substantially within the suprachoroidial space over an avascular region such as the pars plana or a surgically induced avascular region; or in direct communication with the vitreous.

U.S. Pat. No. 5,476,511 to Gwon et al. discloses a polymer implant for placement under the conjunctiva of the eye. The implant may be used to deliver neovascular inhibitors for the treatment of ARMD and drugs for the treatment of retinopathies, and retinitis. The pharmaceutically active agent diffuses through the polymer body of the implant.

U.S. Pat. No. 5,773,019 to Ashton et al. discloses a non-bioerodable polymer implant for delivery of certain drugs including angiostatic steroids and drugs such as cyclosporine for the treatment of uveitis. Once again, the pharmaceutically active agent diffuses through the polymer body of the implant.

All of the above-described implants require careful design and manufacture to permit controlled diffusion of the pharmaceutically active agent through a polymer body or polymer membrane to the desired site of therapy. Drug release from these devices depends on the porosity and diffusion characteristics of the matrix or membrane, respectively. These parameters must be tailored for each drug moiety to be used with these devices. Consequently, these requirements generally increase the complexity and cost of such implants.

U.S. Pat. No. 5,824,073 to Peyman discloses an indentor for positioning in the eye. The indentor has a raised portion that is used to indent or apply pressure to the sclera over the macular area of the eye. This patent discloses that such pressure decreases choroidal congestion and blood flow through the subretinal neovascular membrane, which, in turn, decreases bleeding and subretinal fluid accumulation.

U.S. Pat. Nos. 5,725,493 and 5,830,173 both disclose non-bioerodable implants that have a drug containing reservoir located outside the globe of the eye and a drug delivery tube running from the reservoir and into the vitreous cavity at the pars plana.

Despite the above-described ophthalmic implants, a need still exists for a surgically implantable ophthalmic drug delivery device capable of safe, effective, rate-controlled, delivery of a wide variety of pharmaceutically active agents. The surgical procedure for implanting such a device should be safe, simple, quick, and capable of being performed in an outpatient setting. Ideally, such a device should be easy and economical to manufacture. Furthermore, because of its versatility and capability to deliver a wide variety of pharmaceutically active agents, such an implant should be capable of use in ophthalmic clinical studies to deliver various agents that create a specific physical condition in a patient. Ideally, such an ophthalmic drug delivery device would be capable of localized delivery of pharmaceutically active agents to a specific portion of the retina, as well as pan-retinal delivery of pharmaceutically active agents. In addition, such a device should ideally be suitable for delivering two or more drugs in combination therapy.

SUMMARY OF THE INVENTION

One aspect of the present invention is an ophthalmic drug delivery device having a scleral surface, an orbital surface, an injection port on the orbital surface, and a fluid conducting passageway disposed within the device. The scleral surface has a curvature that facilitates contact with a sclera of an eye. The injection port is for sealingly engaging a needle of a syringe, which is for providing a fluid comprising a pharmaceutically active agent. The fluid conducting passageway is fluidly coupled to the injection port and terminates in an opening for communicating the fluid to an outer surface of the sclera.

BRIEF DESCRIPTION OF THE DRAWINGS

For a more complete understanding of the present invention, and for further objects and advantages thereof, reference is made to the following description taken in conjunction with the accompanying drawings in which.

DETAILED DESCRIPTION OF THE PREFERRED EMBODIMENTS

The preferred embodiments of the present invention and their advantages are best understood by referring to FIGS. 1–10B of the drawings, like numerals being used for like and corresponding parts of the various drawings.

FIGS. 1–4B schematically illustrate an ophthalmic drug delivery device 10 according to a preferred embodiment of the present invention. Device 10 may be used in any case where delivery of a pharmaceutically active agent to the eye is required. Device 10 is particularly useful for delivery of active agents to the posterior segment of the eye. A preferred use for device 10 is the delivery of pharmaceutically active agents to the retina for treating ARMD, choroidial neovascularization (CNV), retinopathies, retinitis, uveitis, macular edema, and glaucoma. Of course, device 10 may also be utilized for the delivery of pharmaceutically active agents to body tissue other than the eye, if desired.

Figure 1:
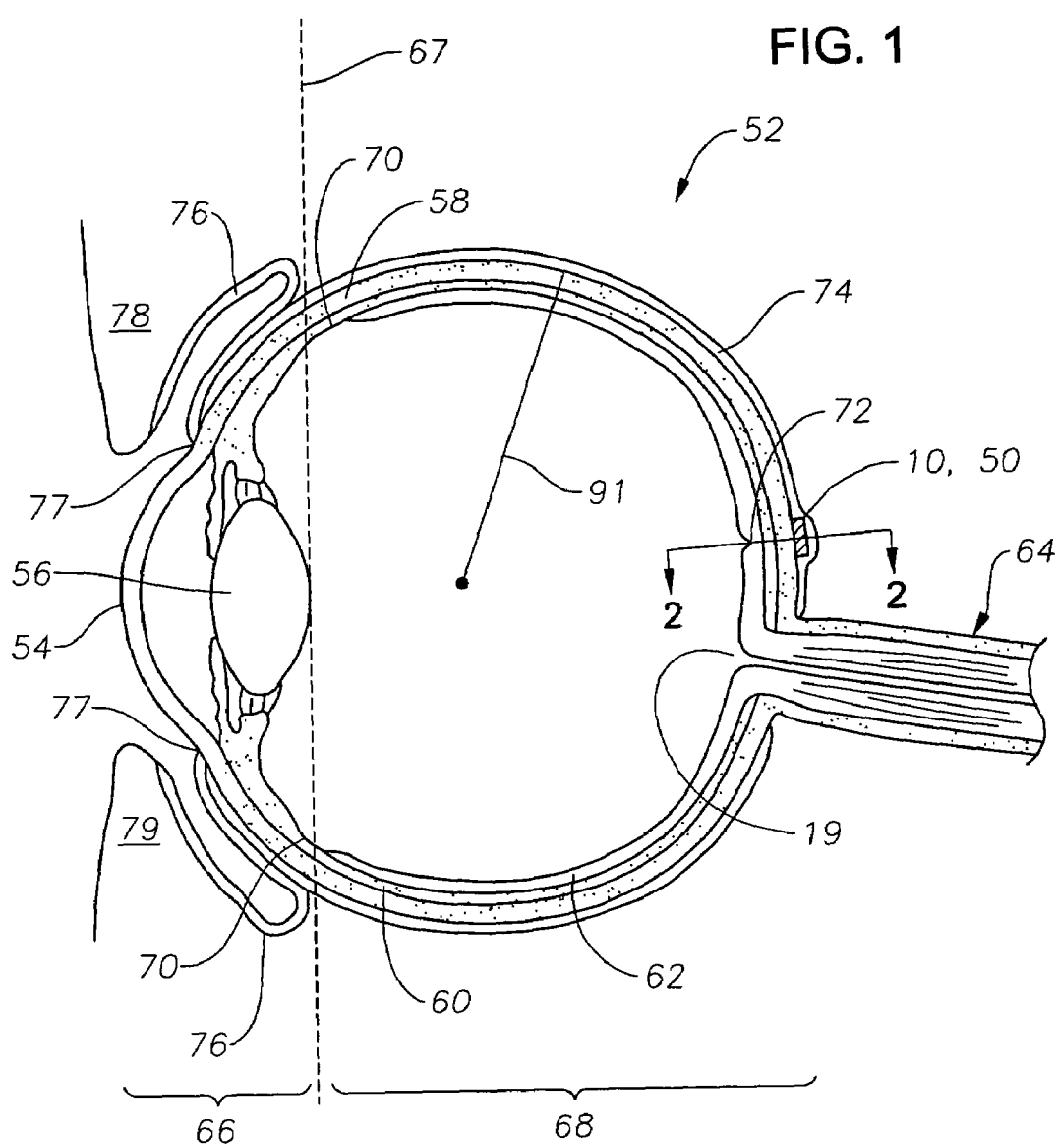
FIG. 1 is a side sectional view schematically illustrating the human eye.
Figure 2:
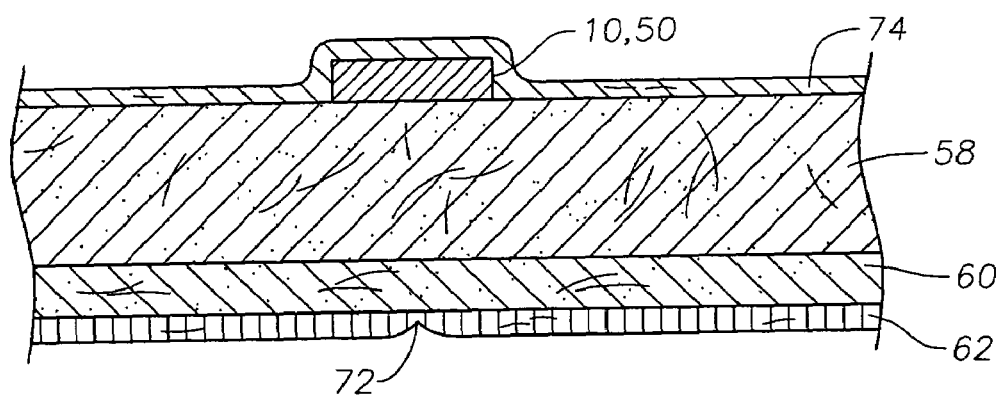
FIG. 2 is detailed cross-sectional view of the eye of FIG. 1 along line 2—2.

Referring to FIGS. 1–2, a human eye 52 is schematically illustrated. Eye 52 has a cornea 54, a lens 56, a sclera 58, a choroid 60, a retina 62, and an optic nerve 64. An anterior segment 66 of eye 52 generally includes the portions of eye 52 anterior of a line 67. A posterior segment 68 of eye 52 generally includes the portions of eye 52 posterior of line 67. Retina 62 is physically attached to choroid 60 in a circumferential manner proximate pars plana 70. Retina 62 has a macula 72 located slightly lateral to its optic disk 19. As is well known in the ophthalmic art, macula 72 is comprised primarily of retinal cones and is the region of maximum visual acuity in retina 62. A Tenon's capsule or Tenon's membrane 74 is disposed on sclera 58. A conjunctiva 76 covers a short area of the globe of eye 52 posterior to limbus 77 (the bulbar conjunctiva) and folds up (the upper cul-de-sac) or down (the lower cul-de-sac) to cover the inner areas of upper eyelid 78 and lower eyelid 79, respectively. Conjunctiva 76 is disposed on top of Tenon's capsule 74.

As is shown in FIGS. 1 and 2, and as is described in greater detail hereinbelow, device 10 is preferably disposed directly on the outer surface of sclera 58, below Tenon's capsule 74 for treatment of most posterior segment diseases or conditions. In addition, for treatment of ARMD in humans, device 10 is preferably disposed directly on the outer surface of sclera 58, below Tenon's capsule 74, with its distal end 92 proximate macula 72.

Figure 3:
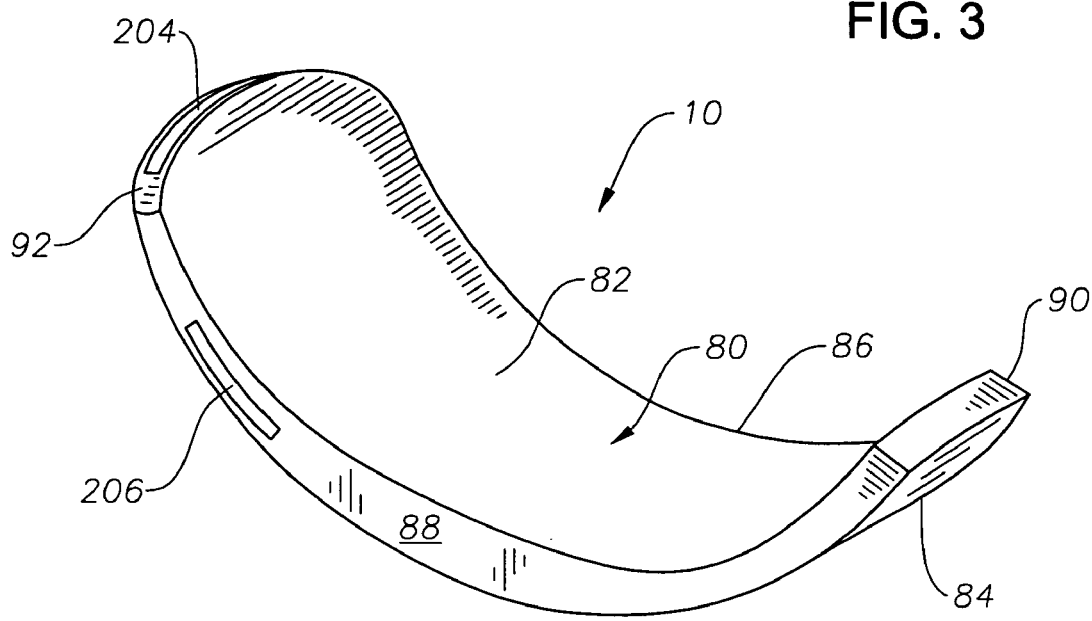
FIG. 3 is a perspective view of an ophthalmic drug delivery device according to a preferred embodiment of the present invention.
Figure 4A:
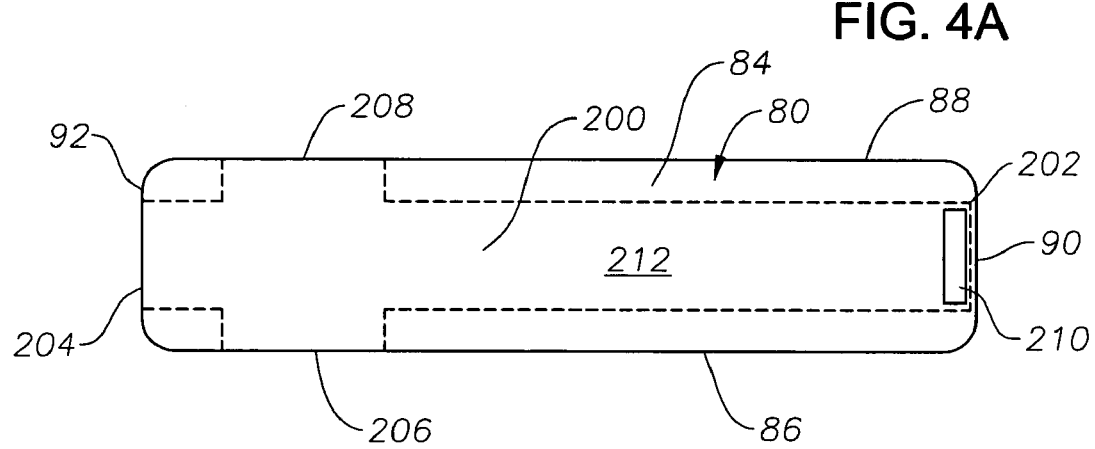
FIG. 4A is an orbital view of the device of FIG. 3 showing a preferred embodiment of the internal fluid conducting passageways of the device.
Figure 4B:
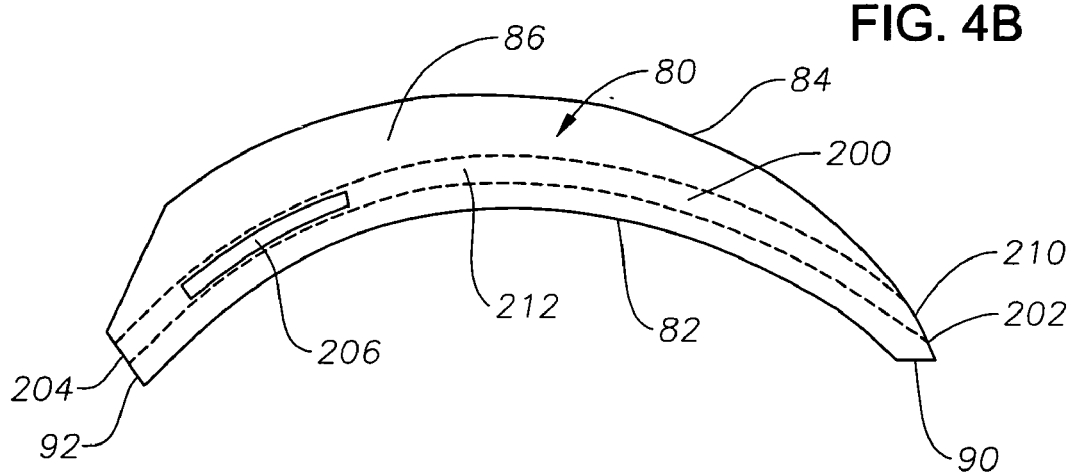
FIG. 4B is a side view of the device of FIG. 4A.
Figure 5:
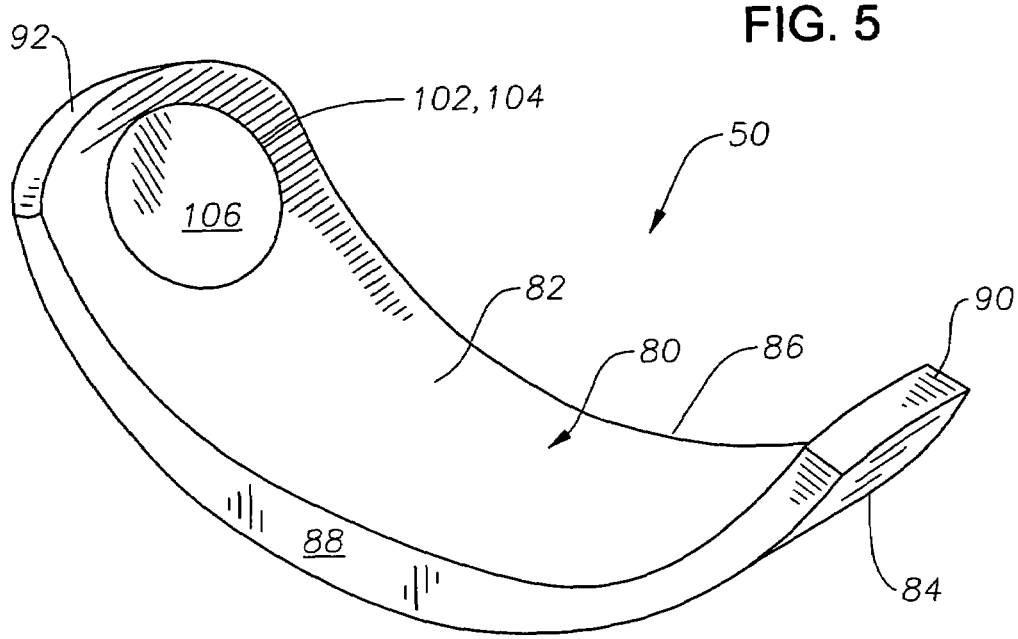
FIG. 5 is a perspective view of an ophthalmic drug delivery device according to a second preferred embodiment of the present invention.
Figure 5A:
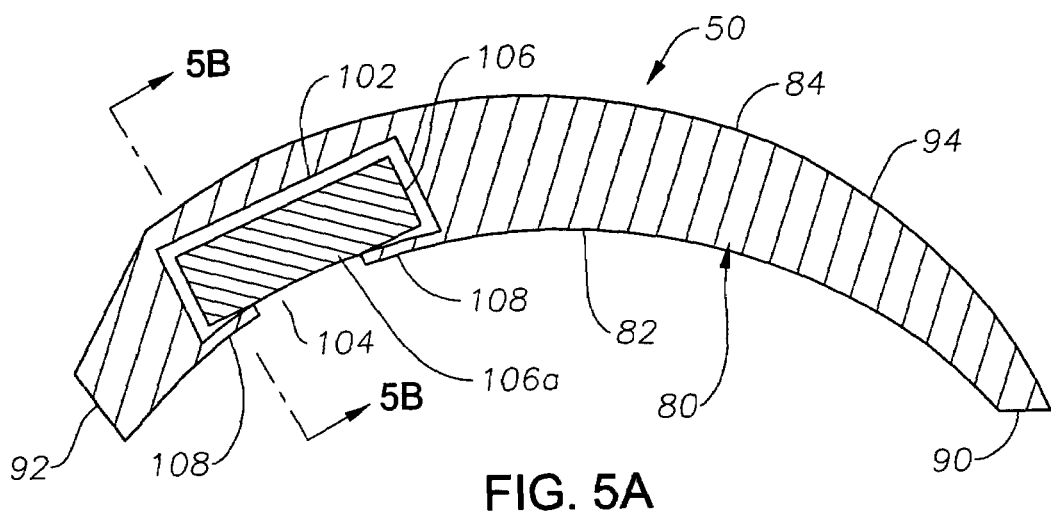
FIG. 5A is a side sectional view of the ophthalmic drug delivery device of FIG. 5 with the internal fluid conducting passageways of the device not shown for clarity of illustration.
Figure 5B:
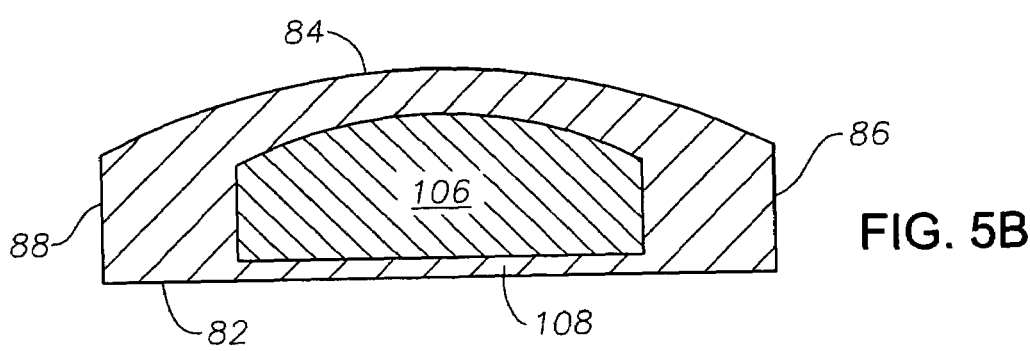
FIG. 5B is an enlarged cross-sectional view of the ophthalmic drug delivery device of FIG. 5A taken along line 5B—5B.

FIGS. 3, 4A, and 4B schematically illustrate device 10 in greater detail. Device 10 generally includes a body 80 having a scleral surface 82 and an orbital surface 84. Scleral surface 82 is preferably designed with a radius of curvature that facilitates direct contact with sclera 58. Most preferably, scleral surface 82 is designed with a radius of curvature equal to the radius of curvature 91 of an average human eye 52. (See FIG. 1) Orbital surface 84 is preferably designed with a radius of curvature that facilitates implantation under Tenon's capsule 74. Body 80 preferably has a curved, generally rectangular three-dimensional geometry with rounded sides 86 and 88, proximal end 90, and distal end 92. Body 80 may have any other geometry that has a curved scleral surface 82 for contact with sclera 58. By way of example, body 80 may have a generally cylindrical, oval, square, or other polygonal three-dimensional geometry.

Body 80 preferably comprises a biocompatible, non-bioerodable material. Body 80 more preferably comprises a biocompatible, non-bioerodable polymeric composition. Said polymeric composition may be a homopolymer, a copolymer, straight, branched, cross-linked, or a blend. Examples of polymers suitable for use in said polymeric composition include silicone, polyvinyl alcohol, ethylene vinyl acetate, polylactic acid, nylon, polypropylene, polycarbonate, cellulose, cellulose acetate, polyglycolic acid, polylactic-glycolic acid, cellulose esters, polyethersulfone, acrylics, their derivatives, and combinations thereof. Examples of suitable soft acrylics are more fully disclosed in U.S. Pat. No. 5,403,901, which is incorporated herein in its entirety by reference. Said polymeric composition most preferably comprises silicone. Of course, said polymeric composition may also comprise other conventional materials that affect its physical properties, including, but not limited to, porosity, tortuosity, permeability, rigidity, hardness, and smoothness. Exemplary materials affecting certain ones of these physical properties include conventional plasticizers, fillers, and lubricants. Said polymeric composition may comprise other conventional materials that affect its chemical properties, including, but not limited to, toxicity and hydrophobicity.

Device 10 has a plurality of fluid conducting passageways or cavities within body 80. FIGS. 4A and 4B show a preferred system of such passageways having a main passageway 200 having a proximal end 202, a distal opening 204, a first side opening 206, and a second side opening 208. Passageway 200 and openings 204, 206, and 208 preferably have a generally rectangular cross-section. Device 10 also has an injection port 210 located on orbital surface 84 of body 80 near proximal end 202 of main passageway 200. Injection port 210 is preferably made of a fluid impervious material that can be penetrated by a needle and that reseals itself upon removal of the needle. A preferred material is silicone rubber. In addition, injection port 210 is preferably colored or marked by raised protuberances. Although not shown in the FIGS. 3–4A, passageway 200 may also have one or more openings to scleral surface 82 of device 10.

A conventional syringe and needle may be used to impart a fluid 212 containing a pharmaceutically active agent or agents into passageway 200 via injection port 210. Fluid 212 may comprise a solution, a suspension, an emulsion, an ointment, a gel forming solution, a gel, a bioerodable polymer, a non-bioerodable polymer, microparticles, or combinations thereof. Most preferably, fluid 212 is a suspension with or without microparticles formed from bioerodable polymers. Fluid 212 includes one or more ophthalmically acceptable pharmaceutically active agents, and may also include conventional non-active incipients. Examples of pharmaceutically active agents suitable for fluid 212 are anti-infectives, including, without limitation, antibiotics, antivirals, and antifungals; antiallergenic agents and mast cell stabilizers; steroidal and non-steroidal anti-inflammatory agents; cyclooxygenase inhibitors, including, without limitation, Cox I and Cox II inhibitors; combinations of anti-infective and anti-inflammatory agents; decongestants; anti-glaucoma agents, including, without limitation, adrenergics, β-adrenergic blocking agents, α-adrenergic agonists, parasypathomimetic agents, cholinesterase inhibitors, carbonic anhydrase inhibitors, and prostaglandins; combinations of anti-glaucoma agents; antioxidants; nutritional supplements; drugs for the treatment of cystoid macular edema including, without limitation, non-steroidal anti-inflammatory agents; drugs for the treatment of ARMD, including, without limitation, angiogenesis inhibitors and nutritional supplements; drugs for the treatment of herpetic infections and CMV ocular infections; drugs for the treatment of proliferative vitreoretinopathy including, without limitation, antimetabolites and fibrinolytics; wound modulating agents, including, without limitation, growth factors; antimetabolites; neuroprotective drugs, including, without limitation, eliprodil; and angiostatic steroids for the treatment of diseases or conditions of posterior segment 68, including, without limitation, ARMD, CNV, retinopathies, retinitis, uveitis, macular edema, and glaucoma. Such angiostatic steroids are more fully disclosed in U.S. Pat. Nos. 5,679,666 and 5,770,592. Preferred ones of such angiostatic steroids include 4,9(11)-Pregnadien- 17α, 21-diol-3,20-dione and 4,9(11)-Pregnadien-17α,21-diol-3, 20-dione-21-acetate. These preferred angiostatic steroids are preferably formulated as a suspension. A preferred non-steroidal anti-inflammatory for the treatment of cystoid macular edema is nepafenac. The conventional non-active excipients may include, but are not limited to, ingredients to enhance the stability, solubility, penetrability, or other properties of fluid 212. In particular, hydrolytic enzymes such as proteases, esterases, hyaluronidases, and collegenases may be utilized to enhance the penetration of the pharmaceutically active agents through natural and newly formed connective tissue that may encapsulate device 10 after implantation. Body 80 is preferably impermeable to fluid 212.

Device 10 may be made by conventional polymer processing methods, including, but not limited to, injection molding, extrusion molding, transfer molding, and compression molding. Preferably, device 10 is formed using conventional injection molding techniques.

Device 10 is preferably surgically placed directly on the outer surface of sclera 58 below Tenon's capsule 74 using a simple surgical technique that is capable of being performed in an outpatient setting. The surgeon first performs a peritomy in one of the quadrants of eye 52. Preferably, the surgeon performs the peritomy in the supero-temporal or infra-temporal quadrant, about 3 mm posterior to limbus 77 of eye 52. Once this incision is made, the surgeon performs a blunt dissection to separate Tenon's capsule 74 from sclera 58, forming an antero-posterior tunnel. Once the tunnel is formed, the surgeon uses forceps to hold device 10 with scleral surface 82 facing sclera 58 and distal end 92 away from the surgeon. The surgeon then introduces device 10 into the tunnel in a generally circular motion to position distal end 92 generally above the desired portion of retina 62. The surgeon then closes the peritomy by suturing Tenon's capsule 74 and conjunctiva 76 to sclera 58. After closing, the surgeon places a strip of antibiotic ointment on the surgical wound. Alternatively, the surgeon may suture proximal end 90 of device 50 to sclera 58 to hold device 10 in the desired location before closure of the tunnel.

In the case of ARMD in the human eye, the surgeon preferably utilizes the above-described technique to position distal end 92 of device 10 in the supero-temporal quadrant of eye 52 directly on the outer surface of sclera 58, below Tenon's capsule 74 with side openings 206 and 208 positioned directly above macula 72. A surgeon may position side openings 206 and 208 of device 10 at this location by moving distal end 92 of device 10 toward macula 72 along a path generally between the lateral and superior rectus muscles. For ARMD, the pharmaceutically active agent of fluid 212 is preferably one of the angiostatic steroids disclosed in U.S. Pat. Nos. 5,679,666 and 5,770,592.

In the case of ARMD in the human eye, the surgeon preferably utilizes the above-described technique to position distal end 92 of device 10 in one of two preferred locations in the infra-temporal quadrant of eye 52. One preferred location is directly on the outer surface of sclera 58, below Tenon's capsule 74, with side openings 206 and 208 positioned proximate to, but not directly above, macula 72. A surgeon may position side openings 206 and 208 of device 10 at this location by moving distal end 92 of device 10 below the inferior oblique muscle in a direction generally parallel to the lateral rectus muscle. A second preferred location is directly on the outer surface of sclera 58, below Tenon's capsule 74, with side openings 206 and 208 positioned directly above macula 72. A surgeon may position side openings 206 and 208 of device 10 at this location by moving distal end 92 of device 10 toward macula 72 along a path generally between the lateral and inferior rectus muscles and below the inferior oblique muscle.

Once device 10 is located in the desired position, the surgeon utilizes a conventional syringe and needle to inject fluid 212 into passageway 200. The surgeon preferably moves lower eyelid 79 downward and instructs the patient to look upward so as to expose proximal end 90 of device 10. Injection port 210 may be visualized beneath the Tenon's capsule and any connective tissue encapsulating device 10 due to its color or raised protuberances. The surgeon sticks the needle of the syringe into injection port 210, injects fluid 212 into passageway 200, and removes the needle from the port 210. Port 210 reseals automatically upon removal of the needle. Fluid 212 is disposed throughout passageway 200, and is in communication with sclera 58 via openings 204, 206, 208, and any openings to scleral surface 82.

It is believed that device 10 can be used to deliver a pharmaceutically effective amount of a pharmaceutically active agent through sclera 58 and choroid 60 into retina 62 for many years, depending on the particular physicochemical properties of the particular fluid 212 and its pharmaceutically active agent employed. Important physicochemical properties include hydrophobicity, solubility, dissolution rate, diffusion coefficient, and tissue affinity. In addition, it is believed that device 10 may be used to deliver both a localized distribution of drug primarily beneath distal end 92 of device 10, or to deliver drug to substantially the entire retina, depending upon the particular fluid 212 and its pharmaceutically active agents and incipients. After passageway 200 no longer contains any fluid 212, a surgeon may refill passageway 200 as described hereinabove. Although not shown in FIGS. 3–4B, device 10 may also include a sharp surface or edge on distal end 92, side 86, or side 88 of body 80. During refilling of passageway 200, the surgeon may move device 10 slightly from side to side and/or posteriorly so that such sharp surfaces or edges pierce any connective tissue that may encapsulate device 10 after implantation. Piercing this connective tissue facilitates proper distribution of fluid 212 via openings 204, 206, and 208. In addition, unlike repetitive sub-Tenon's capsule injections of drug formulations, device 10 minimizes the risk of penetrating the globe of the eye, always results in fluid 212 being distributed below the Tenon's capsule 74 on the outer surface of sclera 58, and results in a reproduceable distribution of fluid 212 on a desired portion of the outer surface of the sclera 58.

Figure 6A:
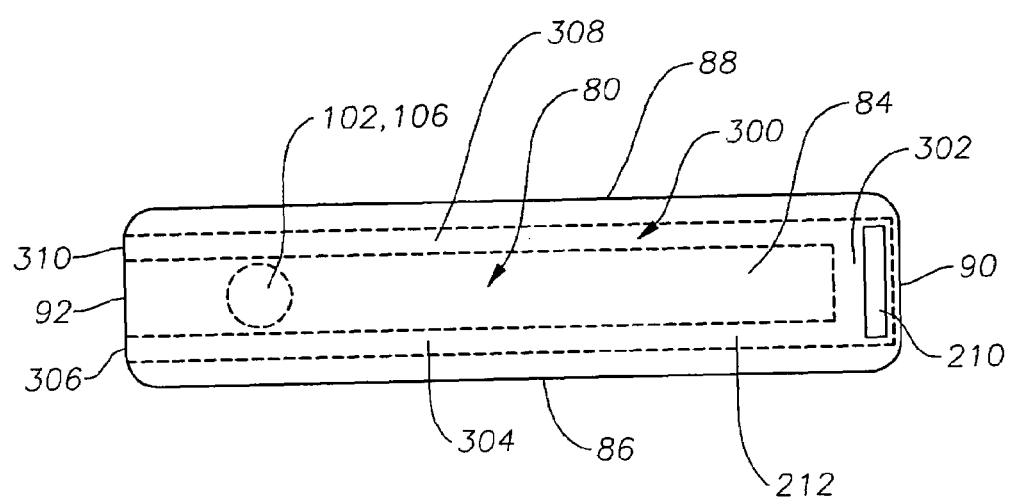
FIG. 6A is an orbital view of the device of FIGS. 5–5B showing a preferred embodiment of the internal fluid conducting passageways of the device.
Figure 6B:
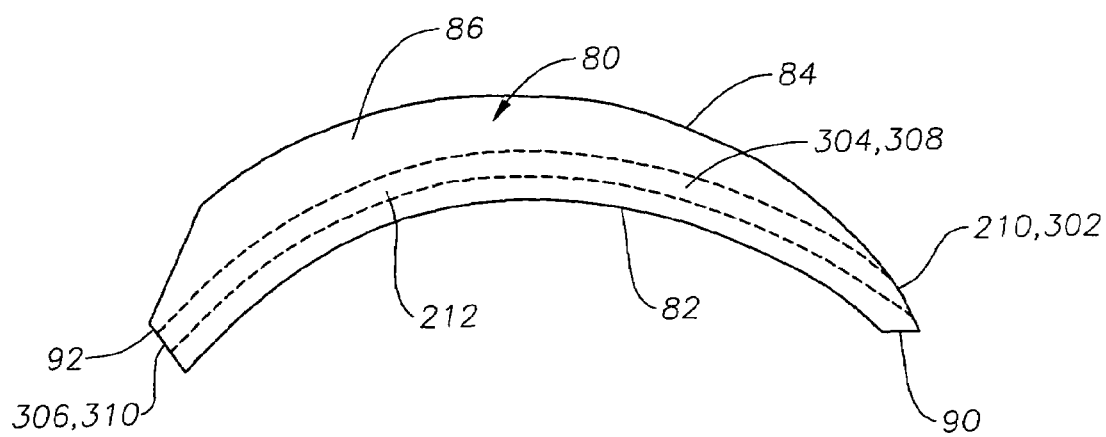
FIG. 6B is a side view of the device of FIG. 6A with the well and inner core of the device not shown for clarity of illustration.

FIGS. 5, 5A, 5B, 6A, and 6B schematically illustrate an ophthalmic drug delivery device 50 according to a second preferred embodiment of the present invention. Device 50 is similar in construction to device 10 described hereinabove, with several important exceptions. First, body 80 of device 50 includes a well or cavity 102 having an opening 104 to scleral surface 82 and holding an inner core 106. Second, device 50 has a preferred system of fluid conducting passageways or cavities 300 within body 80, which is best illustrated in FIGS. 6A and 6B.

Inner core 106 is preferably a tablet comprising one or more pharmaceutically active agents. Alternatively, inner core 106 may comprise a conventional hydrogel having one or more pharmaceutically active agents disposed therein. A retaining member 108 is preferably disposed proximate opening 104. Retaining member 108 prevents inner core 106 from falling out of well 102. When inner core 106 is a cylindrical tablet, retaining member 108 is preferably a continuous rim or lip disposed circumferentially around opening 104 having a diameter slightly less than the diameter of tablet 106. Alternatively, retaining member 108 may comprise one or more members that extend from body 80 into opening 104. Although not shown in FIG. 6A, inner core 106 may alternatively comprise a suspension, solution, powder, or combination thereof containing one or more pharmaceutically active agents. In this embodiment, scleral surface 82 is formed without opening 104, and the suspension, solution, powder, or combination thereof diffuses through the relatively thin portion of scleral surface 82 below inner core 26. Still further in the alternative, device 50 may be formed without well 102 or inner core 106, and the pharmaceutically active agent(s) in the form of a suspension, solution, powder, or combination thereof may be dispersed throughout body 80 of device 50, with the exception of system of passageways 300. In this embodiment, the pharmaceutically active agent diffuses through body 80 into the target tissue.

Body 80 is preferably impermeable to the pharmaceutically active agent of inner core 106. When body 80 is made from a generally elastic polymeric composition, the diameter of well 102 may be slightly less than the diameter of inner core 106. This frictional fit secures inner core 106 within well 102. In this embodiment, body 80 may be formed without retaining member 108, if desired.

The geometry and dimensions of device 50 maximize communication between the pharmaceutically active agent of inner core 106 and the tissue underlying scleral surface 82. Scleral surface 82 preferably physically contacts the outer surface of sclera 58. Although not shown in FIGS. 6A or 6B, inner core 106 may be formed so that surface 106a physically contacts the outer surface of sclera 58. Alternatively, scleral surface 82 may be disposed proximate the outer surface of sclera 58. By way of example, device 50 may be disposed in the periocular tissues just above the outer surface of sclera 58 or intralamellarly within sclera 58.

Inner core 106 may comprise one or more ophthalmically acceptable pharmaceutically active agents. Exemplary pharmaceutically active agents include the pharmaceutically active agents listed hereinabove for fluid 212. Inner core 106 may also comprise conventional non-active excipients to enhance the stability, solubility, penetrability, or other properties of the active agent.

If inner core 106 is a tablet, it may further comprise conventional excipients necessary for tableting, such as fillers and lubricants. Such tablets may be produced using conventional tableting methods. The pharmaceutically active agent is preferably distributed evenly throughout the tablet. In addition to conventional tablets, inner core 106 may comprise a special tablet that bioerodes at a controlled rate, releasing the pharmaceutically active agent. By way of example, such bioerosion may occur through hydrolosis or enzymatic cleavage. If inner core 106 is a hydrogel, the hydrogel may bioerode at a controlled rate, releasing the pharmaceutically active agent. Alternatively, the hydrogel may be non-bioerodable but allow diffusion of the pharmaceutically active agent.

System of passageways 300 preferably comprises a proximal portion 302, a longitudinal portion 304 having an opening 306 on distal end 92 of body 80, and a longitudinal portion 308 having an opening 310 on distal end 92 of body 80. Proximal portion 302 preferably has a generally rectangular cross-section. Longitudinal portions 304 and 308 and openings 306 and 310 preferably have a generally square cross-section. Well 102 and inner core 106 are disposed between longitudinal portions 304 and 308. Injection port 210 is located on orbital surface 84 of body 80 near proximal portion 302. Although not shown in the FIGS. 5–6B, system of passageways 300 may also have one or more openings to scleral surface 82 of device 10. A conventional syringe and needle may be used to impart fluid 212 into system of passageways 300 via injection port 210.

Device 50 may be made by conventional polymer processing methods, including, but not limited to, injection molding, extrusion molding, transfer molding, and compression molding. Preferably, device 50 is formed using conventional injection molding techniques as described hereinabove for device 10.

Device 50 is preferably surgically placed directly on the outer surface of sclera 58 below Tenon's capsule 74 using the simple surgical technique described hereinabove in connection with device 10. In the case of ARMD in the human eye, the surgeon preferably utilizes the above-described technique to position device 50 in the superotemporal quadrant of eye 52 directly on the outer surface of sclera 58, below Tenon's capsule 74, with inner core 106 positioned directly above macula 72. A surgeon may position inner core 106 of device 50 at this location by moving distal end 92 of device 50 toward macula 72 along a path generally between the lateral and superior rectus muscles. For ARMD, the pharmaceutically active agent of inner core 106 is preferably one of the angiostatic steroids disclosed in U.S. Pat. Nos. 5,679,666 and 5,770,592.

In the case of ARMD in the human eye, the surgeon preferably utilizes the above-described technique to position inner core 106 of device 50 in one of two preferred locations in the infra-temporal quadrant of eye 52. One preferred location is directly on the outer surface of sclera 58, below Tenon's capsule 74, with inner core 106 positioned proximate to, but not directly above, macula 72. A surgeon may position inner core 106 of device 50 at this location by moving distal end 92 of device 50 below the inferior oblique muscle in a direction generally parallel to the lateral rectus muscle. A second preferred location is directly on the outer surface of sclera 58, below Tenon's capsule 74, with inner core 106 positioned directly above macula 72. A surgeon may position inner core 106 of device 50 at this location by moving distal end 92 of device 50 toward macula 72 along a path generally between the lateral and inferior rectus muscles and below the inferior oblique muscle.

The physical shape of body 80 of device 50, including the geometry of scleral surface 82, well 102, opening 104, and retaining member 108, facilitate the unidirectional delivery of a pharmaceutically effective amount of the pharmaceutically active agent from inner core 106 through sclera 58, choroid 60, and into retina 62. In particular, the absence of a polymer layer or membrane between inner core 106 and sclera 58 greatly enhances and simplifies the delivery of an active agent to retina 62.

Once device 50 is located in the desired position, the surgeon utilizes a conventional syringe and needle to inject fluid 212 into system of passageways 300 as described hereinabove for device 10. Fluid 212 is disposed throughout proximal portion 302 and longitudinal portions 304 and 308, and is in communication with sclera 58 via openings 306, 310, and any openings to scleral surface 82.

It is believed that device 50 can be used to deliver a pharmaceutically effective amount of a pharmaceutically active agent through sclera 58 and choroid 60 into retina 62 for many years, depending on the particular physicochemical properties of the particular fluid 212, the particular inner core 106, and their pharmaceutically active agents employed. Important physicochemical properties include hydrophobicity, solubility, dissolution rate, diffusion coefficient, and tissue affinity. In addition, it is believed that device 50 may be used to deliver both a localized distribution of drug primarily beneath distal end 92 of device 10, or to deliver drug to substantially the entire retina, depending upon the particular fluid 212, inner core 106, and their pharmaceutically active agents and excipients. After inner core 106 no longer contains active agent, a surgeon may easily remove device 50, if desired. The "pre-formed" tunnel facilitates the replacement of an old device 50 with a new device 50. After passageway 200 no longer contains any fluid 212, a surgeon may refill passageway 200 as described hereinabove.

It should be noted that fluid 212 and inner core 106 may contain the same or different pharmaceutically active agents. Device 50 is especially useful for combination drug therapy, and in this case fluid 212 and inner core 106 contain different pharmaceutically active agents. For example, fluid 212 may contain a pharmaceutically active agent(s) that is most easily or best formulated as a fluid, and inner core 106 may contain a pharmaceutically active agent(s) that is most easily or best formulated as a solid or a semi-solid. In addition, while not wanting to be limited to any particular theory, it is believed that fluid 212 may be best for delivery of drug to substantially the entire retina, while inner core 106 may be best for localized delivery of drug primarily beneath inner core 106.

Figure 7A:
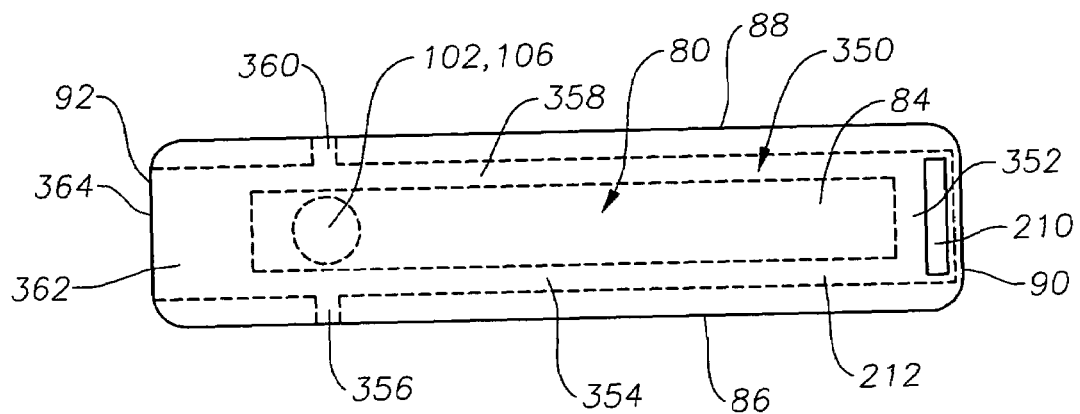
FIG. 7A is an orbital view of the device of FIGS. 5–5B showing a second preferred embodiment of the internal fluid conducting passageways of the device.
Figure 7B:
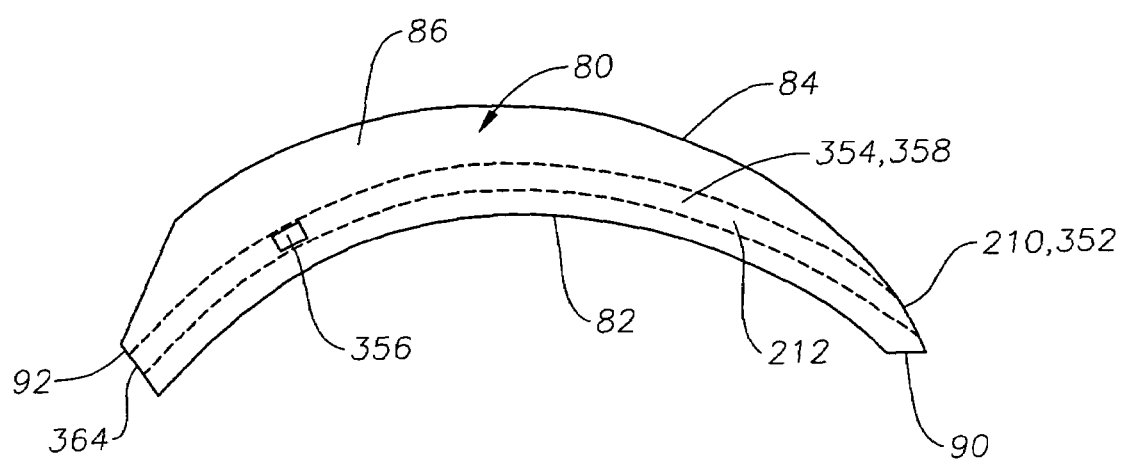
FIG. 7B is a side view of the device of FIG. 7A with the well and inner core of the device not shown for clarity of illustration.

FIGS. 7A and 7B show a second preferred system of fluid conducting passageways or cavities 350 within body 80 of device 50. System of passageways 350 preferably comprises a proximal portion 352, a longitudinal portion 354 having an opening 356 on side 86 of body 80, a longitudinal portion 358 having an opening 360 on side 88 of body 80, and a distal portion 362 having an opening 364 on distal end 92 of body 80. Portions 352 and 362 preferably have a generally rectangular cross-section, and portions 354 and 358 preferably have a generally square cross-section. Opening 364 preferably has a generally rectangular cross-section, and openings 356 and 360 preferably have a generally square cross-section. Well 102 and inner core 106 are surrounded by system of passageways 350. Injection port 210 is located on orbital surface 84 of body 80 near proximal portion 352. Although not shown in the FIGS. 7A–B, system of passageways 350 may also have one or more openings to scleral surface 82 of device 50. A conventional syringe and needle may be used to impart fluid 212 into system of passageways 300 via injection port 210. A device 50 having a system of passageways 350 is constructed, implanted into the eye, and operated in substantially the same manner as described hereinabove with device 50 having a system of passageways 300.

Figure 8A:
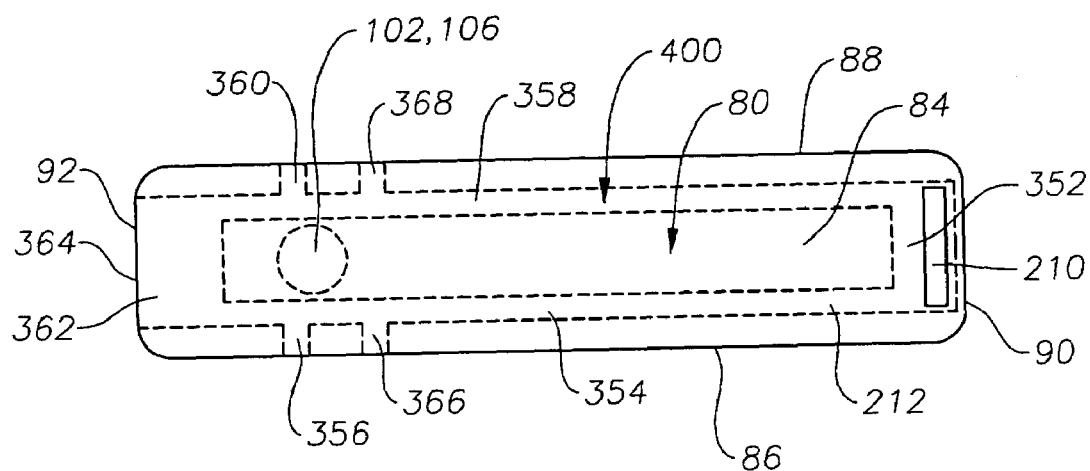
FIG. 8A is an orbital view of the device of FIGS. 5–5B showing a third preferred embodiment of the internal fluid conducting passageways of the device.
Figure 8B:
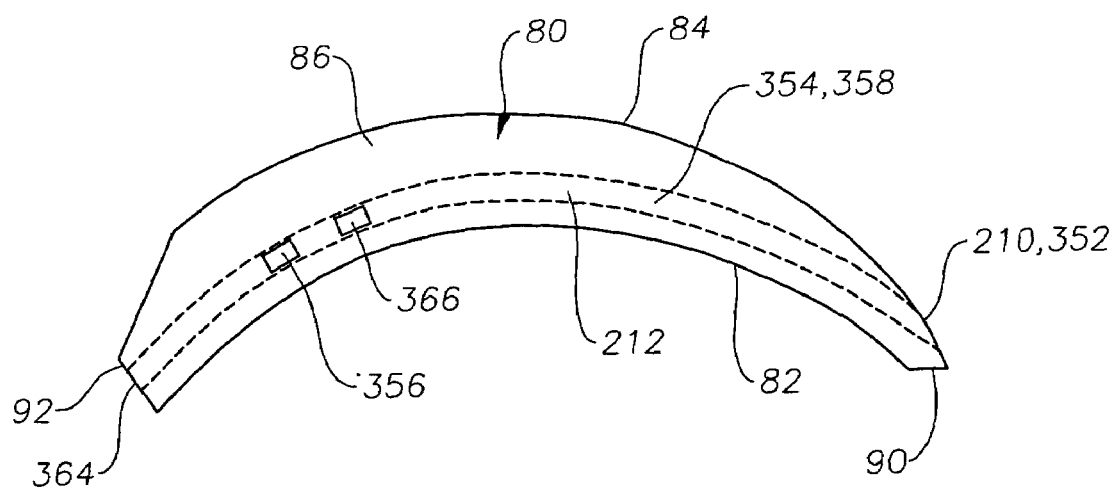
FIG. 8B is a side view of the device of FIG. 8A with the well and inner core of the device not shown for clarity of illustration.

FIGS. 8A and 8B show a third preferred system of fluid conducting passageways or cavities 400 within body 80 of device 50. System of passageways 400 is identical to system of passageways 350 of FIGS. 7A and 7B, with the exception that longitudinal portion 354 has an additional opening 366 on side 86 of body 80, and longitudinal portion 358 has an additional opening 368 on side 88 of body 80. Openings 356, 366, 360, and 368 preferably surround well 102 and inner core 106. Although not shown in FIGS. 8A–B, longitudinal portions 354 and 358 may be formed with more than two such openings, if desired. Although not shown in the FIGS. 8A–B, system of passageways 400 may also have one or more openings to scleral surface 82 of device 50. A device 50 having a system of passageways 400 is constructed, implanted into the eye, and operated in substantially the same manner as described hereinabove with device 50 having a system of passageways 300.

Figure 9A:
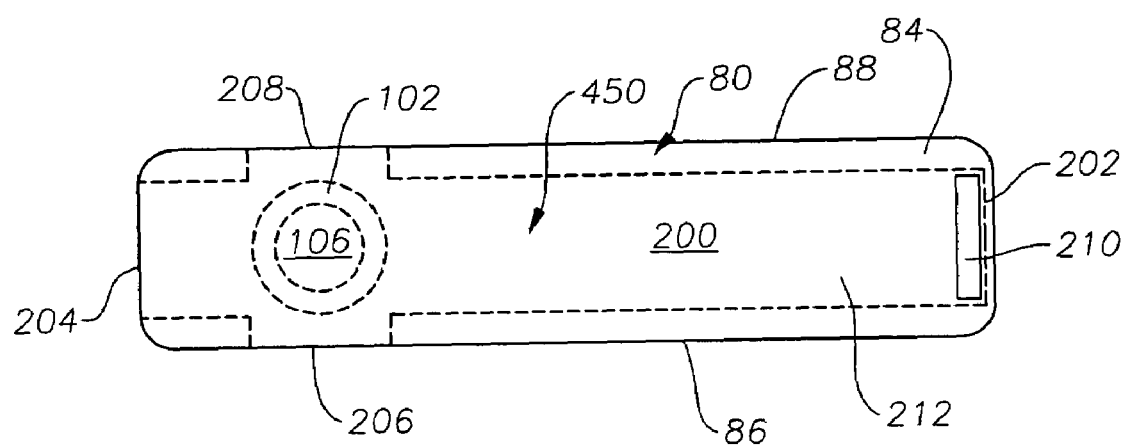
FIG. 9A is an orbital view of the device of FIGS. 5–5B showing a fourth preferred embodiment of the internal fluid conducting passageways of the device.
Figure 9B:
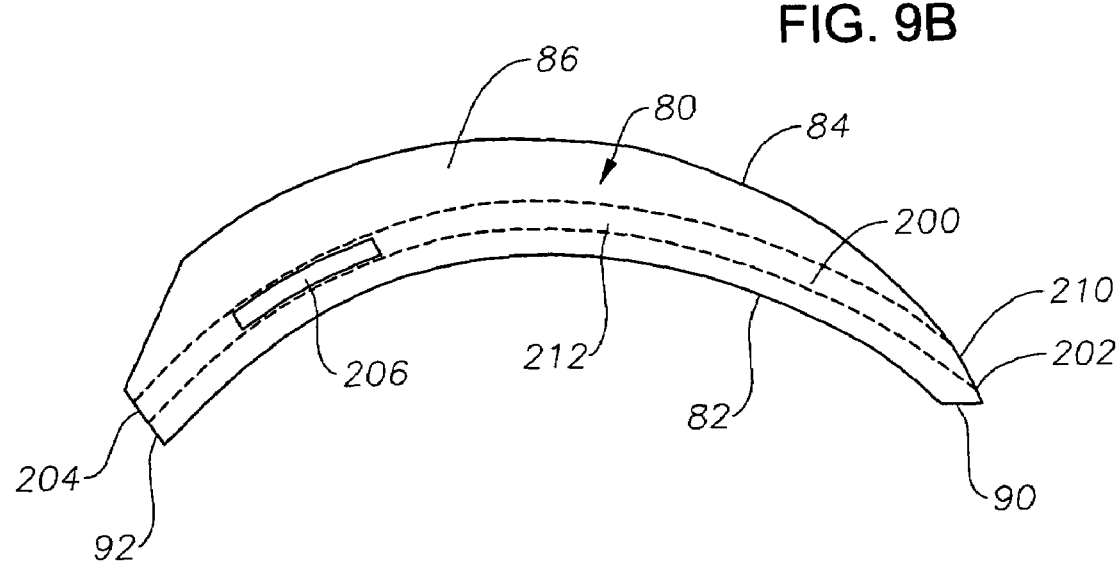
FIG. 9B is a side view of the device of FIG. 9A with the well and inner core of the device not shown for clarity of illustration.

FIGS. 9A and 9B show a fourth preferred system of fluid conducting passageways or cavities 450 within body 80 of device 50. System of passageways 450 is identical to main passageway 200 within body 80 of device 10 of FIGS. 3–4A, with the exception that well 102 is formed within main passageway 200 between first side opening 206 and second side opening 208. Although not shown in the FIGS. 9A–B, system of passageways 450 may also have one or more openings to scleral surface 82 of device 50. A device 50 having a system of passageways 450 is constructed, implanted into the eye, and operated in substantially the same manner as described hereinabove with device 50 having a system of passageways 300.

Figure 10A:
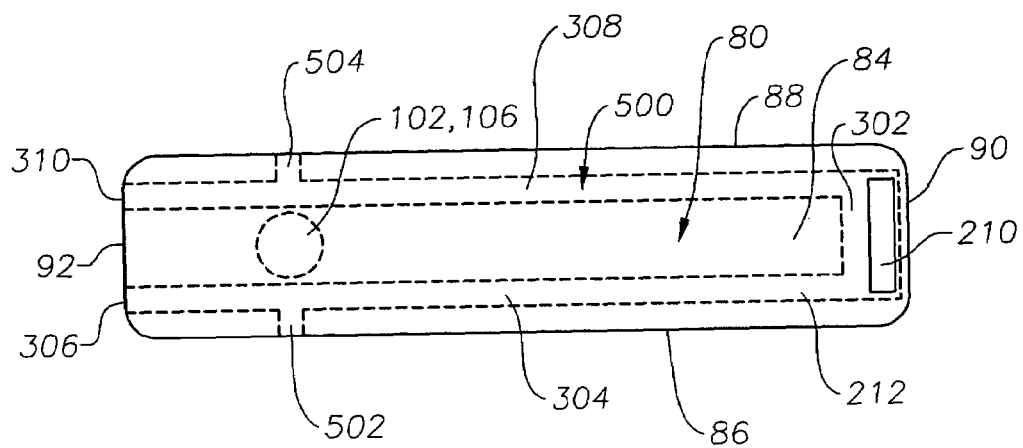
FIG. 10A is an orbital view of the device of FIGS. 5–5B showing a fifth preferred embodiment of the internal fluid conducting passageways of the device.
Figure 10B:
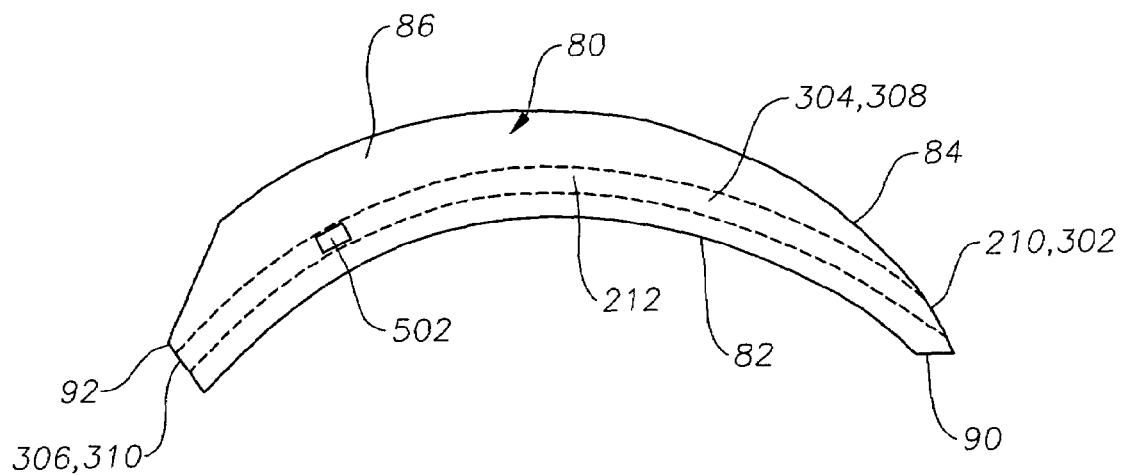
FIG. 10B is a side view of the device of FIG. 10A with the well and inner core of the device not shown for clarity of illustration.

FIGS. 10A and 10B show a fifth preferred system of fluid conducting passageways or cavities 500 within body 80 of device 50. System of passageways 500 is identical to system of passageways 300 of FIGS. 6A and 6B, with the exception that longitudinal portion 304 has an opening 502 on side 86 of body 80, and longitudinal portion 308 has an opening 504 on side 88 of body 80. Although not shown in the FIGS. 10A–B, system of passageways 500 may also have one or more openings to scleral surface 82 of device 50. A device 50 having a system of passageways 500 is constructed, implanted into the eye, and operated in substantially the same manner as described hereinabove with device 50 having a system of passageways 300.

From the above, it may be appreciated that the present invention provides improved devices and methods for safe, effective, rate-controlled delivery of a variety of pharmaceutically active agents to the eye. The devices of the present invention are especially useful for localized and/or pan-retinal delivery of pharmaceutically active agents to the posterior segment of the eye to combat diseases such as ARMD, CNV, retinopathies, retinitis, uveitis, macular edema, and glaucoma. The devices of the present invention are also particularly useful for combination drug therapy. The surgical procedure for implanting the devices is safe, simple, quick, and capable of being performed in an outpatient setting. The devices are easy and economical to manufacture. Furthermore, because of their capability to deliver a wide variety of pharmaceutically active agents, such devices are useful in clinical studies to deliver various agents that create a specific physical condition in a patient or animal subject.

The present invention is illustrated herein by example, and various modifications may be made by a person of ordinary skill in the art. For example, the systems of fluid conducting passageways of the present invention may be employed into the ophthalmic drug delivery devices having a generally F-shaped geometry, a generally C-shaped geometry, or a generally L-shaped geometry as disclosed in U.S. Pat. No. 6,416,777. As another example, well 102 and inner core 106 may have a generally oval, square, or other polygonal three-dimensional geometry. As a further example, different cross-sectional geometries and layouts of fluid conducting passageways and their respective openings may be utilized than described hereinabove.

It is believed that the operation and construction of the present invention will be apparent from the foregoing description. While the apparatus and methods shown or described above have been characterized as being preferred, various changes and modifications may be made therein without departing from the spirit and scope of the invention as defined in the following claims.

What is claimed is:

1. An ophthalmic drug delivery device, comprising:
    a scleral surface having a curvature that facilitates contact with a sclera of an eye;
    an orbital surface;
    an injection port on said orbital surface for sealingly engaging a needle of a syringe, said syringe for providing a fluid comprising a pharmaceutically active agent; and
    a fluid conducting passageway disposed within said device, fluidly coupled to said injection port, and terminating in an opening for communicating said fluid to an outer surface of said sclera.

2. The ophthalmic drug delivery device of claim 1 further comprising a sharp surface on an exterior of said device for piercing connective tissue that may encapsulate said device upon implantation on said outer surface of said sclera.

3. The ophthalmic drug delivery device of claim 1 wherein said fluid conducting passage terminates in a plurality of openings for communicating said fluid to said outer surface of said sclera.

4. The ophthalmic drug delivery device of claim 1 further comprising a plurality of said fluid conducting passageways.

5. The ophthalmic drug delivery device of claim 1 further comprising:
    a well having a second opening to said scleral surface;
    an inner core disposed in said well and comprising a second pharmaceutically active agent.

6. The ophthalmic drug delivery device of claim 5 wherein said pharmaceutically agent and said second pharmaceutically active agent are identical.

7. The ophthalmic drug delivery device of claim 5 wherein said pharmaceutically active agent is different from said second pharmaceutically active agent.

8. The ophthalmic drug delivery device of claim 7 wherein said pharmaceutically agent is formulated as a fluid, and said second pharmaceutically active agent is formulated as a solid or semi-solid.

9. The ophthalmic drug delivery device of claim 5 wherein:
    said fluid delivers said pharmaceutically active agent through said sclera and a choroid into a retina of said eye; and
    said inner core delivers said second pharmaceutically active agent through said sclera and a choroid into a retina of said eye.

10. The ophthalmic drug delivery device of claim 9 wherein said fluid delivers said pharmaceutically active agent to substantially all of said retina, and said inner core delivers said second pharmaceutically active agent to a portion of said retina disposed generally beneath said inner core.

11. The ophthalmic drug delivery device of claim 1 further comprising a second pharmaceutically active agent disposed in said device outside of said fluid conducting passageway, wherein said second pharmaceutically active agent diffuses through said device.

12. The ophthalmic drug delivery device of claim 11 wherein said pharmaceutically agent and said second pharmaceutically active agent are identical.

13. The ophthalmic drug delivery device of claim 11 wherein said pharmaceutically active agent is different from said second pharmaceutically active agent.

* * * * *